Jan. 16, 1940. H. F. YODER Plant Pat. 354
ROSE
Filed March 4, 1939
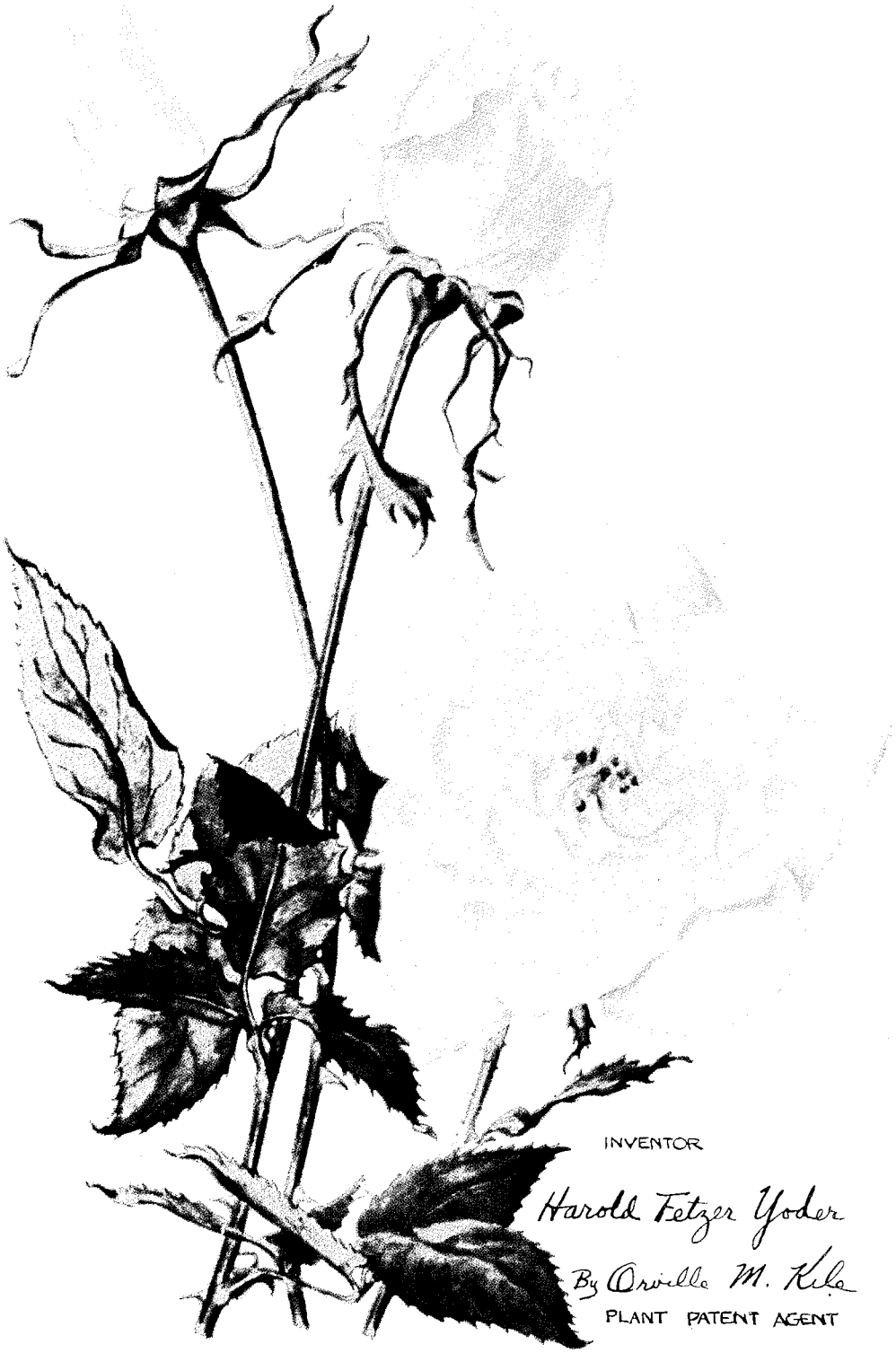

Patented Jan. 16, 1940

UNITED STATES PATENT OFFICE

354

ROSE

Harold Fetzer Yoder, Barberton, Ohio, assignor to Yoder Brothers, Barberton, Ohio Application March 4, 1939, Serial No. 259,867

1 Claim. (Cl. 47—61)

The new variety is a sport of "Mrs. Franklin D. Roosevelt" and was discovered by me in Yoder Brothers' greenhouses as a single branch on the parent plant. It has since been reproduced asexually, retaining its distinguishing characteristics. This new variety differs from its parent principally in color, length of bud, more foliaceous sepals, and strength of growth.

The original illustrations accompanying this application depict three specimens of this new variety in various stages of opening, in approximately their true coloring and size.

Following is a detailed description of this new variety. Color plate references are to Ridgway's Color Standards and Nomenclature. The ordinary dictionary term is intended when no plate references are indicated.

*The plant*

Growth:

Upright bush. Growth stronger and more vigorous than that of its parent.

*Stems.*—Long, straight; Oil Green (Plate V). Thorns occur on stems.

*Peduncle.*—Very long and slender, with many fine white spines.

*Thorns.*—Numerous; irregularly placed, large, long, slender and very sharp; white or with pinkish tinge; extend almost at right angles to stem, sometimes slightly downward-pointing.

*Spines.*—Numerous fine spines are found on the peduncle.

*Foliage.*—Plentiful but not large. Leaves—composed of 3 to 7 leaflets. Leaflets:—Color—medium green, being approximately Dark Cress Green (Plate XXXI), on the upper surface. Shape—ovate with acute apex. Margin—sharply serrate. Size—terminal leaflets 2½ to 3 inches by 1¼ to 1½ inches wide. Lateral leaflets vary in size, the pair next the stem usually being quite small. Substance—not particularly heavy.

*Rachis.*—Slender, smooth, short, grooved above.

*Stipules.*—Slender, clinging, medium length.

*Sepals.*—Long and somewhat foliaceous. In opening bud they stand at right angles to stem, making a frame for the bud. Later they turn completely backward. Outside surface and leaflike portions are same color as leaves. Inside surface much lighter and covered with fuzz.

Blooming habit:

Flowers borne singly on long stems. Free and continuous bloomer.

*The flower*

Bud:

*Size.*—Just before opening averages 1½ inches in length.

*Shape.*—Long, slender and pointed.

*Opening.*—Rapid but even.

*Color.*—Between Jasper Red and Eugenia Red (Plate XIII), with a large base of Apricot Yellow (Plate IV).

Blossom:

*Form.*—First cup-shaped, then petals spread showing the large center composed of many stamens and pistils. When blossom is fully open the petals turn backward, partially quilled and puffed.

*Size.*—Medium—3½ to 4½ inches across.

*Petalage.*—In January about 25 petals, including 4 or 5 petaloids. Petals:—Shape—oval, usually with slight point at top. Size—outer petals 1½ by 1¾ inches. Substance—outer row of petals has rather heavy substance, but inner petals are not quite so heavy. Color—the under surface of outer petals is between Coral Red (Plate XIII) and Jasper Red (Plate XIII), with some spots of Eugenia Red (Plate XIII) which are the portions visible in the opening bud. The inner surface of the outer petals is between Light Coral Red (Plate XIII) and Light Jasper Red (Plate XIII). The outer surface of the inner petals is approximately the same color as the inner surface of the outer row of petals. The inner surface of the inner petals is much lighter and tempered with yellow, being approximately Ochraceous-Buff to Ochraceous-Salmon (Plate XV). All the petals have a large base of yellow which diffuses upward into the red and salmon shades. On the outer surface of the petals this base is Apricot Yellow (Plate IV); on the inner surface it is Lemon Chrome (Plate IV) and is larger than on the outer surface.

The color is rather evenly distributed over the petals and its intensity of shade varies somewhat in different specimens. The color effect in the early stages of opening is almost uniform in a shade between Jasper Red and Eugenia Red (Plate XIII), except for the base of yellow. As the flower opens the two-toned effect becomes evident as the inner surface of the petals becomes visible. As it opens further and only the inner surface of the petals is visible, the effect is then of an Ochraceous-Buff (Plate XV) to Ochraceous-Salmon (Plate XV) rose with a frame of outer petals in shades of dull pink to red which would fall approximately in the range between Jasper Pink and Light Jasper Red (Plate XIII). As the flower ages, the color changes slightly so that then the center petals seem to contain a slight brushing of pink and the outer petals tend somewhat toward Deep Rose Pink (Plate XII).

*Behavior.*—Petals drop cleanly.

*Longevity.*—Medium.

*Fragrance.*—Has definite tea fragrance with a slight cinnamon tendency.

*Reproductive organs*

Pistils:
Many, bunched, uneven in length.
*Stigma.*—Light yellow.
*Style.*—White with reddish tinge just below stigma.

Stamens:
Many, bunched around pistils. Uneven lengths but longer than pistils.
*Filaments.*—Brilliant yellow.
*Anthers.*—Yellow with brown edge; large.

Ovary:
Large.

Having thus disclosed my discovery I claim;

A new and distinct variety of hybrid tea rose substantially as shown and described, characterized particularly by its exceedingly long slender bud; its pleasing fragrance combining the odors of cinnamon and tea; its strong bush growth; and its two-toned blossoms combining tones from Light Coral Red to Eugenia Red with tones from Ochraceous-Buff to Ochraceous-Salmon.

HAROLD FETZER YODER.